United States Patent [19]

Seckinger et al.

[11] Patent Number: 4,666,502

[45] Date of Patent: May 19, 1987

[54] HERBICIDAL N-THIENYL-CHLOROACETAMIDES

[75] Inventors: Karl Seckinger, Riegel; Fred Kuhnen, Weil, both of Fed. Rep. of Germany; Karlheinz Milzner, Basel, Switzerland

[73] Assignee: Sandoz Ltd., Basel, Switzerland

[21] Appl. No.: 463,581

[22] Filed: Feb. 3, 1983

[30] Foreign Application Priority Data

Feb. 9, 1982 [GB] United Kingdom ............... 8203636
Sep. 13, 1982 [GB] United Kingdom ............... 8226006

[51] Int. Cl.$^4$ .................. A01N 43/10; A01N 43/82; C07D 333/36; C07D 419/12

[52] U.S. Cl. ........................... 71/90; 71/88; 71/92; 71/95; 544/333; 548/122; 548/123; 548/124; 548/125; 548/127; 548/128; 548/131; 548/134; 548/136; 548/143; 548/171; 548/181; 548/183; 548/187; 548/195; 548/206; 548/209; 548/213; 548/214; 548/221; 548/226; 548/229; 548/233; 548/241; 548/243; 548/245; 548/246; 548/255; 548/262; 548/305; 548/309; 548/318; 548/336; 548/337; 548/359; 548/364; 548/374; 548/375; 548/465; 548/517; 548/518; 548/527; 548/557; 548/558; 549/34; 549/38; 549/39; 549/60; 549/63; 549/69; 549/431; 549/448; 549/449; 549/473; 549/478; 549/480

[58] Field of Search ............... 549/69, 480, 63, 478, 549/479; 71/90, 88; 548/213, 214, 244, 245

[56] References Cited

U.S. PATENT DOCUMENTS

| | | | |
|---|---|---|---|
| 2,576,106 | 11/1951 | Cusic | 549/69 |
| 2,929,702 | 3/1960 | Speziale | 71/90 |
| 3,014,046 | 12/1961 | Speziale | 549/69 |
| 3,133,808 | 5/1964 | Hamm | 71/88 |
| 3,442,945 | 5/1969 | Olin | 71/118 |
| 3,547,620 | 12/1970 | Olin | 71/118 |
| 3,705,910 | 12/1972 | Lundberg et al. | 71/90 |
| 3,823,161 | 7/1974 | Lesser | 549/69 |
| 3,937,730 | 2/1976 | Vogel et al. | 71/118 |
| 4,021,224 | 5/1977 | Pallos et al. | 71/90 |
| 4,240,820 | 12/1980 | Dickore et al. | 549/69 |
| 4,282,028 | 8/1981 | Ziman | 71/90 |
| 4,317,915 | 3/1982 | Confalone et al. | 549/68 |
| 4,472,425 | 9/1984 | Sandmeier et al. | 549/63 |

FOREIGN PATENT DOCUMENTS

| | | | |
|---|---|---|---|
| 767244 | 11/1971 | Belgium | 549/69 |
| 613501 | 1/1961 | Canada | 71/88 |
| 2276 | 1/1982 | Japan . | |
| 781702 | 8/1957 | United Kingdom | 71/88 |
| 1497536 | 12/1974 | United Kingdom | 71/88 |
| 1548397 | 7/1979 | United Kingdom | 548/214 |

OTHER PUBLICATIONS

Hamm and Speziale, Agricultural and Food Chemistry, vol. 4, No. 6, Jun. 1956.

*Primary Examiner*—Henry R. Jiles
*Assistant Examiner*—Kurt G. Briscoe
*Attorney, Agent, or Firm*—Gerald D. Sharkin; Richard E. Vila

[57] ABSTRACT

The invention provides 5-membered heteroaromatic compounds of formula I $$ArN(Y)COCH_2Cl \qquad I$$

wherein Ar is a 5-membered heteroaromatic group comprising 1 or 2 heteroatoms selected from O, S and N and linked by a ring C-atom to the N-atom of the $N(Y)COCH_2Cl$ group to which it is bound, whereby where Ar is pyrazolyl, said $N(Y)COCH_2Cl$ group is in the 4-position,
and Y is as specified in the description, the use of these compounds as herbicides, compositions for facilitating such use and the preparation of the chloroacetamides.

25 Claims, No Drawings

HERBICIDAL N-THIENYL-CHLOROACETAMIDES

The present invention relates to novel 5-membered heteroaromatic compounds bearing at one ring C-atom a N-substituted chloroacetylamino group, their use as herbicides, agricultural compositions for facilitating such use and the preparation of the novel compounds of the invention.

Various herbicidal N-substituted α-halogenacetanilides are known.

The U.S. Pat. No. 4,282,028 discloses N-substituted-N-2,5-dialkyl-pyrrol-1-yl)haloacetamides having herbicidal and plant-growth-regulating activity. The need exists for still more effective herbicides. The novel 5-membered heteroaromatic compounds are particularly effective herbicides having an appropriate soil persistence.

The present invention provides compounds of formula I

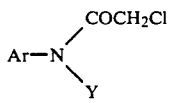

wherein

Ar is a 5-membered heteroaromatic group comprising 1 or 2 ring heteroatoms selected from O, S and N, and linked by a C-ring atom to the N-atom of the N(Y)-COCH$_2$Cl group to which it is bound, whereby, where Ar is pyrazolyl, said N(Y)COCH$_2$Cl group is in the 4-position, and Y is allene, CH$_2$-CH=C=CH$_2$, or is a hydrocarbon selected from C$_{1-8}$alkyl, C$_{3-8}$alkenyl, C$_{3-8}$alkinyl, C$_{3-8}$cycloalkyl, C$_{5-8}$cycloalkenyl, C$_{3-8}$cycloalkyl-C$_{1-5}$alkyl, whereby such hydrocarbon is unsubstituted or substituted by halogen selected from F, Cl or Br; or is a group CH(R$_1$)-COY$_1$, wherein R$_1$ is H or C$_{1-5}$alkyl and Y$_1$ forms together with the CO-group to which it is bound an ester or amide function; or is a group R$_2$-A$_z$, wherein R$_2$ is CH$_2$ or CH$_2$-CH$_2$ unsubstituted or substituted by C$_{1-5}$alkyl and Az is an aromatic heteroring selected from a di- or triazole linked by one of its nitrogen atoms to R$_2$, a 5-membered heteroring linked by a C-atom of said ring to R$_2$ and having 1 to 3 heteroatoms selected from the group consisting of O, S or N, and a pyrimidine group, or is a 2-oxo-1-pyrrolidinyl group in which one CH$_2$ group can be replaced by O, S or NCH$_3$ and 5-oxo- and/or bicyclic benz[c] fused derivatives of such 2-oxo-1-pyrrolidinyl group or is a group A—O-R$_3$, wherein R$_3$ is H, hydrocarbon selected from the group consisting of C$_{1-8}$alkyl, C$_{3-8}$alkenyl, C$_{3-8}$alkinyl, C$_{3-8}$cycloalkyl, C$_{5-8}$cycloalkenyl or C$_{3-8}$cycloalkyl-C$_{1-5}$alkyl, whereby the hydrocarbon is unsubstituted or substituted; or a group

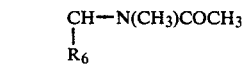

wherein

R$_4$ is hydrocarbon selected from C$_{1-5}$alkyl, C$_{3-5}$alkenyl, C$_{3-5}$alkinyl, C$_{3-8}$cycloalkyl, C$_{5-8}$cycloalkenyl, C$_{3-8}$cycloalkyl-C$_{1-5}$alkyl, whereby the hydrocarbon is unsubstituted or substituted by halogen selected from F, Cl or Br; or is allene R$_4'$ is H or has one of the meanings defined for R$_4$ and A is a hydrocarbon moiety, which may be linked with R$_3$ to form a saturated oxygen containing heterocyclic ring comprising 1 or 2 oxygens as heteroatom, and whereby the N and O atoms to which it is bound are separated by up to 3 C-atoms; or is a group

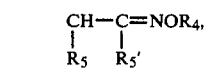

wherein

R$_4$ is as defined above,

R$_5$ and R$_5'$ are independently H or CH$_3$ or

R$_5$ together with R$_5'$ are (CH$_2$)$_3$ or (CH$_2$)$_4$ or is a group

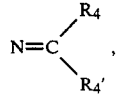

wherein

R$_6$ is H or C$_{1-3}$alkyl.

The Ar group may be unsubstituted or substituted. Where Ar is substituted it may bear substituents in any possible position; preferred positions of such substituents are in o-position, particularly in o,o'-position of the chloroacetamide group, whereby additional substituents may be present. Examples of suitable substituents of Ar are halogen selected from F, Cl and Br; C$_{1-4}$alkyl unsubstituted or substituted by halogen (F, Cl, Br), C$_{1-4}$alkoxy or C$_{3-6}$cycloalkyl; C$_{2-4}$alkenyl unsubstituted or substituted by C$_{1-4}$alkoxy; C$_{3-6}$cycloalkyl; formyl or C$_{2-4}$alkanoyl and functional derivatives such as oximes, acetals and ketals thereof (e.g. C(=NOC$_{1-4}$alkyl)-C$_{1-3}$alkyl, C(O-C$_{1-4}$alkyl)$_2$-C$_{1-3}$alkyl, CH(O-C$_{1-4}$alkyl)$_2$ etc.); C$_{1-4}$alkyl-S, C$_{1-4}$alkyl-SO, C$_{1-4}$alkyl-SO$_2$; C$_{1-5}$alkoxy-carbonyl; C$_{1-4}$alkoxy unsubstituted or substituted by halogen or C$_{1-4}$alkoxy; C$_{2-4}$alkenyloxy, C$_{2-4}$alkinyloxy; hydroxy and hydroxymethyl and esters thereof (e.g. esters with an organic carboxylic acids, for example formic acid, a C$_{2-5}$alkane carboxylic acid or an halogenated derivative thereof, such as acetic acid or chloroacetic acid).

Any optional substituent(s) of Ar which is not in o-position of the N-substituted chloroacetylamino group is preferably selected from C$_{1-4}$alkyl (e.g. CH$_3$), halogen (e.g. Cl, Br) and C$_{1-4}$alkoxycarbonyl (e.g. COOCH$_3$).

Where Ar contains 2 ring heteroatoms, one of them is N; the other is preferably selected from O or S.

A preferred sub-group of compounds of formula I, are compounds wherein Ar contains either one ring heteroatom (pyrrolyl, thienyl, furanyl) or 2 adjacent ring heteroatoms (isoxazolyl, isothiazolyl, pyrazolyl). The N-substituted chloroacetylamino group is preferably tied to the ring C-atom in β-position of the ring heteroatom(s); thus in the 3-position where Ar is pyrrol, thiophene or furan and in the 4-position where Ar is isoxazole, isothiazole or pyrazole. A preferred sub-group of the latter group are those compounds wherein the Ar-group is substituted in ortho-, more preferably in ortho-ortho'-position of the N-substituted acetylamino group, especially when the substituent(s) are selected from the group specified hereinbefore. Any ring N-atom may be unsubstituted or substituted; where it is substituted, it is preferably substituted by $C_{1-4}$alkyl, especially $CH_3$ or $C_2H_5$. Ar signifies preferably a thiophene, isothiazole and isoxazole, more preferably isothiazole or thiophene ring. A particularly preferred sub-group of compounds of formula I, are compounds wherein Ar is thiophene, particularly 3-thienyl which is at least 2,4-disubstituted, especially those 3-thienyl compounds wherein the substituents in 2- and 4-position are selected from $C_{1-4}$alkyl and $C_{1-4}$alkoxy.

Where Y, $R_3$, $R_4$ and $R_4'$ are hydrocarbon substituted by halogen, such halogen is preferably Cl or Br; any such substituted hydrocarbon is particularly monosubstituted. Where Y is halogen substituted hydrocarbon, the halogen is in general preferably not in the 1-position where the use as herbicide is intended (such 1-halogenated compounds are in general unstable; they are however useful as valuable intermediates for the production of other compounds of formula I, e.g. for those wherein Y is alkoxyalkyl or pyrazolylmethyl); a suitable example of such significance of Y is 2-Cl-ethyl.

Where Y, $R_3$, $R_4$ and/or $R_4'$ are $C_{1-8}$alkyl, $C_{3-8}$alkenyl or $C_{3-8}$alkinyl, they preferably have up to 5 C-atoms. Where Y, $R_3$, $R_4$ and/or $R_4'$ are or contain cycloalkyl or cycloalkenyl such cyclic hydrocarbon groups contain preferably up to 6 C-atoms.

Where $R_1$ is $C_{1-5}$alkyl it is preferably $CH_3$ or $C_2H_5$, particularly $CH_3$. The term ester or amide function used in connection with the meaning of $Y_1$ is intended to embrace any function obtainable by the reaction of the COOH group of an acid with any organic compound reacting with such acid with the elimination of water e.g. an alcohol, an amine, a mercaptan, an oxime, a hydrazine, hydrazide or hydrazone. Examples of suitable ester significances of $Y_1$ are $C_{1-5}$alkoxy-CO, $C_{3-5}$alkinyl-O-CO etc. Examples of suitable amide significances of $Y_1$ are $C_{1-4}$alkylamino-CO, di($C_{1-4}$alkyl)amino-CO, CO-NHNH$_2$ and CO-NH-N=C($C_{1-3}$alkyl)$_2$.

Where $R_2$ is $CH_2$ it may be substituted by 1 or 2, preferably 1 $C_{1-5}$alkyl. Where $R_2$ is $CH_2CH_2$ it may be substituted by up to 4 $C_{1-5}$alkyl group and is preferably mono- or disubstituted. Where $CH_2CH_2$ is disubstituted, the substituents are preferably at different C-atoms.

Preferred $C_{1-5}$alkyl substituents of $R_2$ are $CH_3$ and $C_2H_5$, particularly $CH_3$. Where $R_2$ is substituted by $C_{1-5}$alkyl, it is preferably monosubstituted. $R_2$ is especially $CH_2$ or $CH(CH_3)$.

Where Az is one of the above defined aromatic heterorings, such ring may be unsubstituted or substituted; suitable substituents of such Az significances are e.g. one or more $C_{1-5}$alkyl (such as $CH_3$, $C_2H_5$) groups; such substituted aromatic heterorings are preferably mono- or di-substituted.

Where Az is di- or triazole it is preferably 1-pyrazolyl, 1-imidazolyl, 1,2,3-triazol-1-yl or 1,2,4-triazole-1-yl, unsubstituted or substituted, particularly 1-pyrazolyl, 3,5-di-$CH_3$-1-pyrazolyl.

Where Az is the above defined 5-membered heteroring linked by a ring C-atom to $R_2$, such ring is e.g. a furyl, a thienyl, a thiazolyl, an isothiazolyl, an oxazolyl, an isoxazolyl, a 1,2,4- or 1,3,4-thia- or oxadiazol or a 1,3,4-triazolyl group, unsubstituted or substituted, e.g. by one or two substituents of the group $C_{1-4}$alkyl, $C_{1-4}$alkylthio, $C_{1-4}$alkoxy; typical examples of such significances are 2-furyl, 2-thienyl, 2-$CH_3$-4-thiazolyl, 3-$CH_3$-5-isoxazolyl, 2-$C_2H_5$-1,3,4-oxadiazol-5-yl, 3-$CH_3$-1,2,4-oxadiazol-5-yl, 1-$CH_3$-2-$CH_3$S-1,3,4-triazol-5-yl and 2-$CH_3$-1,3,4-triazol-5-yl.

Where Az is a pyrimidine group, this may be linked by its 2-, 4- or 5-C-atom to $R_2$, and is e.g. 2-pyrimidinyl.

Where Az is the above defined bicyclic 2-oxo-1-pyrrolidinyl derivative, the benzo-moiety may be unsubstituted or substituted, e.g. by halogen; a suitable example of such significance is 2-oxo-1,3-benzothiazol-3-yl and the 4-chloro derivative thereof.

Where $R_3$ is the above defined hydrocarbon, such hydrocarbon may be unsubstituted or substituted, e.g. by halogen, cyano, an azole group such as 1-pyrazolyl and/or by $C_{1-4}$alkoxy; such substituted hydrocarbon significance of $R_3$ are preferable monosubstituted. Examples of such $R_3$ significances are $CH_2CH_2Cl$, (1-pyrazolyl)-$CH_2$, $CH_2CH_2CN$, 3,5-dimethyl-1-pyrazolyl.

Suitable meanings of A-O-$R_3$, when A is linked with $R_3$ to form a ring, are e.g. 1,3-dioxolane-4-yl—$C_{1-3}$alkylene, 1,3-dioxolane-2-yl-$C_{1-3}$alkylene and 2- or 3-tetrahydrofuryl-$C_{1-3}$alkylene.

Where A is not linked with $R_3$ to form a ring, A is preferably a non-aromatic, particularly a $C_{1-8}$alkylene moiety separating the O- and N-atom to which it is bound by 1 to 3, preferably 1 or 2 C-atoms. A suitable significance of A is a $CH_2$ or $CH_2$-$CH_2$ group or monomethylated derivatives thereof, particularly $CH_2$, $CH(CH_3)$, $CH_2CH_2$ and $CH(CH_3)CH_2$; $R_3$ is then especially $C_{1-3}$alkyl, such as $CH_3$, $C_2H_5$ and $nC_3H_7$.

A may be unsubstituted or substituted, e.g. by $C_{1-5}$alkoxy. Any substituted A significance is preferably mono-substituted.

The present invention also provides processes for producing a compound of formula I comprising
(a) substituting in a compound of formula II

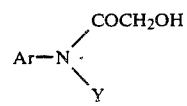

wherein Ar and Y are as defined above,
the HO group of the N-hydroxyacetyl group by Cl,
(b) reacting a compound of formula III

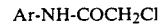    III wherein Ar is as defined above,
with a compound of formula IV

LY    IV wherein
Y is as defined above, and
L is a leaving group capable of being splitt off under the N-alkylation reaction conditions,
(c) obtaining a compound of formula Ia

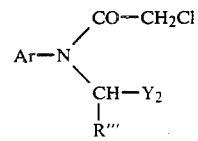    Ia wherein
R''' is H or C$_{1-3}$alkyl,
Y$_2$ is Az', OR$_3$,N(CH$_3$)COCH$_3$ and
Az' is a di- or triazole linked by one of its nitrogen atoms to CHR''' and
Ar and R$_3$ are as defined above,
by reacting a compound of formula V

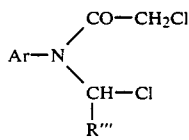   V wherein Ar and R''' are as defined above,
with a reactive derivative of a compound of formula VI

   VI wherein Y$_2$ is as defined above,
(d) N-acylation of a compound of formula VII Ar-NH-Y   VII wherein Ar and Y are as defined above,
with chloroacetyl chloride, or a reactive functional derivative thereof.

Process (a) of the invention can be carried out by conventional manner under conditions known for the substitution of an OH group by a Cl.

Such substitution can for example be effected by treating a compound of formula II with a chlorinating agent, such as thionyl chloride under conditions known per se for analogous reactions.

According to a variante of this chlorination process, the compounds of formula II are first converted into the corresponding sulphonyloxy derivatives, e.g. by O-sulphonation with the aid of a sulphonyl halide, and such sulphonyloxy derivatives then converted into the desired compounds of formula I by nucleophilic substitution of the sulphonyloxy group by chlorine.

Reactants supplying the Cl anions required for such nucleophilic substitution are e.g. alkalimetal chlorides such as NaCl, quaternary tetrabutylammonium chloride or 4-dimethylaminopyridinehydrochloride. Such substitution is conveniently carried out in CH$_2$Cl$_2$ or in an aqueous/organic two-phase system, wherein the organic phase is e.g. a hydrocarbon such as toluene, in the presence of a suitable phase transfer catalyst, preferably with heating e.g. at 40° to 120° C.

Process (b) may be carried out by conventional manner under conditions known for the N-alkylation of amides. The reaction is advantageously carried out in a solvent which is inert under the reaction conditions e.g. dimethoxyethane or acetonitrile or in an aqueous/organic two-phase system in the presence of a phase transfer catalyst.

Suitable meanings of L (in formula IV) are Cl, Br or the sulphonyloxy moiety of an organic sulphonic acid such as mesyloxy or p-tosyloxy.

The compounds of formula III are preferably used in salt form, more preferably in alkalimetal salt form, e.g. the sodium salt form. Such salts are obtained in conventional manner by reaction of the compound of formula III with a base such as an alkalimetal amide, hydride, hydroxide or alcoholate.

For the preparation of compounds of formula Ia according to process (c), the compounds of formula V are suitably used in the form of the alkalimetal salt, e.g. as sodium salt. Where Y$_2$ is a di- or triazole, the compound of formula V may also be used as N-tri-alkylsilyl (e.g. N-trimethylsilyl) compound. The reaction can be effected in conventional manner.

The reaction of process (d) can likewise be effected in conventional manner, under conditions known for the N-chloroacetylation of amines. Where ClCOCH$_2$Cl is used as N-chloroacetylation agent such reaction is conveniently carried out in the presence of an acid binding agent, such as K$_2$CO$_3$.

The compounds of formula I may be recovered from the reaction mixture in which it is formed by working according to established procedures.

It will be appreciated that interconversion of one compound of the invention to another, e.g. conversion of an acid group to an ester group, of a carbonyl group to an oxime, of a haloalkyl group to an ether group (or vice versa) etc., may be carried out in conventional manner. As will also be appreciated, the compounds of the invention may possess one or more asymmetric centres and may therefore exist in optically active, diasteromeric, racemic or geometric isomer forms. In general such compounds are employed as mixtures in the herbicide method and compositions of the invention, even through separation may be effected by known procedures.

The compounds of formulae II, III, V and VII are novel and are part of the invention.

The compounds of formula II may be obtained by ammonolysis of an ester of the compounds of formula VIII ArNHCOCH$_2$OH   VIII wherein Ar is as defined above, with a carboxylic acid, and subsequent introduction of the group Y (as defined above) in the compounds of formula VIII by N-alkylation. Such esters are obtained by acylation of the corresponding compounds of formula IX ArNH$_2$   IX wherein Ar is as defined above, with the appropriate ester of HO-CH$_2$COCl, e.g. with CH$_3$CO-OCH$_2$-COCl.

The compounds of formula III may also be obtained by acylation of a compound of formula IX with chloroacetyl chloride.

Compounds of formula V (which are in fact a subgroup of compounds of formula I) may be obtained by reaction of a compound of formula IX with an appropriate aldehyde and reaction of the Schiff base thus obtained with chloroacetyl chloride.

The compounds of formula VII may be obtained by N-alkylation of a compound of formula IX. Such alkylation can be carried out in conventional manner, with the corresponding alkylating agents (e.g. halogenides), or where appropriate, reductively via the Schiff base or amide.

Many of the compounds of formula IX are novel.

A particular group of valuable novel compounds of formula IX are 3-aminothiophenes substituted in 2- and 4-position by a group selected from C$_{1-4}$alkyl and C$_{1-4}$alkoxy (compounds of formula IXa. The compounds of formula IXa also form part of the invention.

The compounds of formula IX may be obtained by reduction of the corresponding NO$_2$ compounds, e.g. by catalytic hydrogenation under hydrogen pressure in the presence of palladium. Compounds of formula IXa having a $CH_3$ group in 2- or 4-position may be obtained by reduction of the corresponding thiophene-carboxylate with the aid of a complex hydride such as sodium bis(methoxyethoxy)aluminium hydride. Where appropriate, the compounds of formula IXa may also be obtained from the corresponding carbamates esters, e.g. the benzyl carbamate, by hydrolysis. The carbamates, used as starting material, may for example be obtained starting from the corresponding acids, via their azides followed by a Curtius reaction.

Insofar as the production of starting material is not described herein, these compounds are known, or may be produced and purified in accordance with known processes or in a manner analogous to processes described herein or to known processes.

The compounds of formula I are useful because they control or modify the growth of plants. By plants it is meant germinating seeds, emerging seedlings and established vegetation including underground portions.

In particular, the compounds are useful as herbicides as indicated by i.a. the damage caused to both monocotyledoneous and dicotyledoneous plants such as *Lepidium sativum, Avena sativa, Agrostis alba* and *Lolium perenne* in tests by test dosages equivalent to an application rate of from 1.4 to 5.6 kg/ha after pre- or post-emergence application. In view of their herbicidal effect the compounds of the invention are indicated for use in combatting dicotyledoneous and grassy weeds, as confirmed by further evaluation with representative compounds with test dosages equivalent to an application rate of from 0.2 to 5.0 kg active ingredient, e.g. test dosages equivalent to a rate of 0.2, 1.0 and 5.0 kg active ingredient/ha, in dicotyledoneous weeds such as *Amaranthus retroflexus, Capsella bursa-pastoris, Chenopodium alba, Stellaria media, Senecio vulgaris* and *Galium aparine,* and, especially, grassy weeds such as *Agropyron repens, Agrostis alba, Alopecurus myosuroides, Apera spica-venti, Avena fatua, Echinochloa crus-galli, Bromus tectorum, Sorghum halepense, Digitaria spp* and Setaria spp. Additional tests indicate a favourable soil persistence of the compounds of the invention.

The compounds of the invention are relatively less toxic towards crops than towards weeds. Selective herbicidal activity is i.a. observed in corn (maize), soybean, cotton, sugar beet, potato, alfalfa, sunflower, rape, peanuts or flax, depending i.a. on the compound involved and on the application rate. The compounds of the invention are therefore also indicated for use as selective herbicides in a crop locus.

The present invention therefore also provides a method of combatting weeds in a locus, preferably in a crop locus, particularly in a crop locus as mentioned above, which comprises applying to the locus a herbicidally effective amount (a selective herbicidally effective amount where the locus is a crop locus) of a compound of the invention. A particularly preferred and advantageous embodiment of the invention is the pre-emergence (both crops and weeds) use of a compound of formula I in selectively combatting weeds in a crop locus.

For general herbicidal as well as for selective herbicidal use of compounds of the invention, the amount to be applied to attain the desired effect will vary depending on the particular crop if employed for selective use and other standard variables such as the compound employed, mode of application, conditions of treatment and the like. The appropriate application rates can be determined by routine procedures by those skilled in the art, or by comparing the activity of the compounds of the invention with standards for which the application rate is known, e.g. in greenhouse tests. However, in general, satisfactory resutls are usually obtained when the compound is applied at a rate in the range of from about 0.1 to 5 kg/ha, preferably from about 0.2 to 4 kg/ha, more preferably from 0.5 to 3.0 kg/ha, the application being repeated as necessary. When used in a crop locus, the application rate should preferably not exceed 3 kg/ha.

The compounds of formula I may be and preferably are employed as herbicidal compositions in association with herbicidally acceptable diluent(s). Suitable formulations contain 0.01% to 99% by weight of active ingredient, from 0 to 20% herbicidally acceptable surfactant and 1 to 99.99% solid or liquid diluent(s). Higher ratios of surfactant to active ingredient are sometimes desirable and are achieved by incorporation into the formulation or by tank mixing. Application forms of composition generally contain between 0.01 and 25% by weight of active ingredient. Lower or higher levels of active ingredient can, of course, be present depending on the intended use and the physical properties of the compound. Concentrate forms of composition intended to be diluted before use generally contain between 2 and 90%, preferably between 10 and 80% by weight of active ingredient.

Useful formulations of the compounds of the invention include dusts, granules, pellets, suspension concentrates, wettable powders, emulsifiable concentrates and the like. They are obtained by conventional manner, e.g. by mixing the compounds of the invention with the diluent(s). More specifically liquid compositions are obtained by mixing the ingredients, fine solid compositions by blending and, usually grinding, suspensions by wet milling and granules and pellets by impregnating or coating (preformed) granular carriers with the active ingredient or by agglomeration techniques.

Alternatively, the compounds of the invention may be used in microencapsulated form.

Herbicidally acceptable additives may be employed in the herbicidal compositions to improve the performance of the active ingredient and to reduce foaming, caking and corrosion.

Surfactant as used herein means a herbicidally acceptable material which imparts emulsifiability, spreading, wetting, dispersibility or other surface-modifying properties. Examples of surfactants are sodium lignin sulphonate and lauryl sulphate.

Diluents as used herein mean a liquid or solid herbicidally acceptable material used to dilute a concentrated material to a usable or desirable strength. For dusts or granules it can be e.g. talc, kaolin or diatomaceous earth, for liquid concentrate forms, for example a hydrocarbon such as xylene or an alcohol such as isopropanol, and for liquid application forms i.a. water or diesel oil.

The compositions of this invention can also comprise other compounds having biological activity, e.g. compounds having similar or complementary herbicidal activity or compounds having antidotal, fungicidal or insecticidal activity.

Specific Examples of herbicidal compositions will now be described.

EXAMPLE A

Wettable Powder

25 Parts of a compound of formula I, e.g. Compound No. 25 hereinafter given, are mixed and milled with 25 parts of synthetic fine silica, 2 parts of sodium lauryl sulphate, 3 parts of sodium ligninsulphonate and 45 parts of finely divided kaolin until the mean particle size is about 5 micron. The resulting wettable powder is diluted with water before use to a spray liquor with the desired concentration.

EXAMPLE B

Emulsion Concentrate

20 Parts of a compound of formula I, e.g. Compound No. 25 hereinafter given, 40 parts of xylene, 30 parts of dimethyl formamide and 10 parts of emulsifier (e.g. ATLOX 4851 B a blend of Ca alkylarylsulphonate and a polyethoxylated triglyceride of Atlas Chemie GmbH) are throughly mixed until a homogeneous solution is obtained. The resulting emulsion concentrate is diluted with water before use.

EXAMPLE C

Granules

5 Kg of a compound of formula I, e.g. Compound No. 25 hereinafter given, are dissolved in 25 l methylene chloride. The solution is then added to 95 kg of granulated attapulgite (mesh size 24/48 mesh/inch) and thoroughly mixed. The solvent is then evaporated off under reduced pressure.

The invention is further illustrated by the following Examples wherein temperatures are in °C., pressures are in Torr and Rf values are on silica gel, so far not otherwise indicated.

FINAL COMPOUNDS

Example 1

N-(2,4-dimethyl-thien-3-yl)-N-(1,3-dioxolane-2-ylmethyl)-chloroacetamide (process a)

To the well stirred mixture of 1.7 g (0.0063 mol) of N-(2,4-dimethyl-thien-3-yl)-N-(1,3-dioxolane-2-ylmethyl)-hydroxyacetamide, 58 mg of benzyltriethylammonium chloride, 7 ml of toluene and 7 ml of 30% NaOH are added dropwise without cooling 1.31 g (0.0069 mol) of p-toluene sulfonyl chloride in 3.5 ml of toluene. After the exothermic reaction has subsided, stirring is continued for a further 20 hours at ambient temperature.

The toluene layer is then separated, washed with water and dried over anhydrous $Na_2SO_4$.

The crude residue left on rotevaporation of the solvennt is recrystallised from diethyl ether to give N-(2,4-dimethyl-thien-3-yl)-N-(1,3-dioxolane-2-ylmethyl)-tosyloxyacetamide ("tosylate") having a m.p. of 101°–103°.

A stirred mixture of 2.16 g (0.0051 mol) of said tosylate, 1.84 g (0.0066 mol) of tetrabutylammonium chloride, 8 ml of water and 16 ml of toluene is heated at 90° over a period of 6 hours. The toluene layer is then separated, dried ($Na_2SO_4$) and evaporated in vacuo.

The residue is chromatographed on a silica gel column. Elution with hexane-ethylacetate 2:1 affords the title compound as analytically pure crystals, having a m.p. of 76°–78°.

EXAMPLE 2

N-(2,4-dimethyl-thien-3-yl)-N-methoxyethyl-chloroacetamide (process a)

To a stirred solution of 2.0 g (0.008 mol) of N-(2,4-dimethyl-thien-3-yl)-N-methoxyethyl-hydroxyacetamid and 0.92 g (0.008 mol) of 4-dimethylaminopyridine (=DMAP) in 80 ml of dry methylene chloride are added without cooling 0.93 g (0.008 mol) of mesyl chloride in 20 ml of dry $CH_2Cl_2$.

The resulting mixture containing DMAP-hydrochloride and the methanesulphonate of the starting compound is heated under reflux for 25 hours and then evaporated in vacuo.

The residual oil, after column chromatography on silica gel (elution with diethylether), solidified on chilling at −20°, m.p. 54°–55°.

EXAMPLE 3

N-(chloroacetyl)-N-(2-carbomethoxy-4-methyl-thien-3-yl)-alanine-ethylester (process b)

To a well stirred suspension of 1.5 g (0.05 mol) sodium hydride (80% dispersion in mineral oil) in 250 ml of dry dimethoxyethane (=DME) are added portionwise, 9.9 g (0.04 mol) of solid N-(2-carbomethoxy-4-methyl-thien-3-yl)-chloroacetamide.

After the addition is completed the resulting solution of the Na-salt is stirred an additional hour at 50°, then allowed to reach room temperature and treated with the solution of 7.25 g (0.04 mol) of ethyl-2-bromopropionate in 50 ml of dry DME.

After a reaction period of 4 hours at 50°, the mixture is filtered and evaporated in vacuo (50°/0.01 Torr.). The residual brown oil, after chromatography on silica gel (elution with diethyl ether-hexane 2:1), is subjected to ball tube distillation, giving the analytically pure title compound, b.p. 135°/0.005 Torr.

EXAMPLE 4

N-(1H-pyrazol-1-ylmethyl)-N-(2,4-dimethyl-thien-3-yl)-chloroacetamide (process b)

To a well stirred mixture of 19.35 g (0.095 mol) of N-(2,4-dimethyl-thien-3-yl)-chloroacetamide, 4.15 g (0.01 mol) of benzyldimethylhexadecyl-ammonium chloride, 40 g (1 mol) of sodium hydroxide, 200 ml of methylene chloride and 40 ml of water are added 17 g (0.11 mol) of solid 1-chloromethyl pyrazolehydrochloride at such a rate, that the temperature does not rise above 25°.

When the addition is completed, the reaction mixture is stirred an additional 2½ hours at ambient temperature. Then 100 ml of water are added. The organic layer is separated, washed with three 200 ml portions of water, dried over $Na_2SO_4$ and evaporated to dryness. The residue is chromatographed on a silica gel column. Elution with hexane-diethylether 1:1 affords the title compound as an analytically pure syrup which crystallized on chilling overnight at −20°, m.p. 88°–89° (recrystallized from diethyl ether).

EXAMPLE 5

N-(chloroacetyl)-N-(3,5-dimethyl-isoxazol-4-yl)-alanineethylester (process b)

9.4 g (0.05 mol) of N-(3,5-dimethyl-isoxazol-4-yl)-chloroacetamide in 150 ml of dry acetonitrile (=$CH_3CN$) are added dropwise to a well stirred suspension of 1.8 g (0.06 mol) of sodium hydride (80% dispersion in mineral oil) in 25 ml of dry $CH_3CN$.

After the exothermic reaction (34°) has subsided the solution of the sodium salt is allowed to reach room temperature and then treated with the solution of 9.05 g (0.05 mol) of ethyl 2-bromopropionate in 25 ml of dry $CH_3CN$.

After the addition is completed the reaction mixture is heated at 50° for three hours and then evaporated to dryness. The residue is taken up with 100 ml of diethyl ether and filtered. The residual oil left on evaporating the filtrate is chromatographed on a silica gel column. Elution with diethylether-hexane 1:1 affords the title compound, having a m.p. of 49°–50°.

EXAMPLE 6

N-[1-(1H-pyrazol-1-yl)ethyl]-N-(2,4-dimethyl-thien-3-yl)-chloroacetamide (process c)

To a stirred solution of 12.7 g (0.1 mol) of 2,4-dimethyl-3-amino-thiophene in 100 ml of dry benzene, which contains 16 g of molecular sieves (3 Å) and two drops of conc. $H_2SO_4$, are added dropwise 8.5 ml (0.15 mols) of acetaldehyde, taking care that the temperature does not rise above 25°.

When all the acetaldehyde has been introduced, the reaction mixture is stirred 24 hours longer at ambient temperature and is then filtered. Removal of the solvent leaves the Schiff base as a light brown liquid.

To the stirred solution of 13 g (0.085 mols) of this material in 75 ml of dry toluene are added dropwise at −30° 9.7 g (0.086 mols) of chloroacetyl chloride.

When the addition is complete, the reaction solution is stirred for a further 30 minutes at −30° and then treated dropwise at the same temperature with 12 g (0.085 mols) of 1-trimethylsilylpyrazole. After the addition, the solid $CO_2$/acetone bath is removed, the mixture allowed to warm to ambient temperature and left to stir for a further period of 20 hours.

The reaction mixture is then filtered and evaporated in vacuo. The residual syrup is chromatographed on a silica gel column. Elution with hexane/diethyl ether 3:2 affords colourless crystals of the title compound which, upon recrystallization from diethyl ether have a melting point of 76°–78°.

EXAMPLE 7

N-(4-methoxy-2-methyl-thien-3-yl)-N-(2-ethoxyethyl)-chloroacetamide (process d)

To a well stirred mixture of 6,05 g (0.03 mol) N-(2-ethoxyethyl)-4-methoxy-2-methyl-thiophene-3-amine, 4.15 g (0.03 mol) of $K_2CO_3$, 10 ml of water and 100 ml of $CH_2Cl_2$ is added dropwise without cooling the solution of 3.4 g (0.03 mol) of chloroacetyl chloride in 10 ml of $CH_2Cl_2$. After the exothermic reaction (27°) has subsided, stirring is continued for a further hour at ambient temperature.

The methylene chloride layer is then separated, washed twice with 100 ml of water, dried ($Na_4SO_4$) and evaporated in vacuo. The residual crude title compound is analytically pure; RF=0.23 (hexane-diethyl ether 1:2). A small portion of this material was subjected to ball tube distillation: b.p. 168°–170°/0.05 Torr.

The following compounds of formula I are obtained according to one or more of the procedures of the Examples 1 to 7, as indicated hereinbefore: (Me is $CH_3$ and Et is $C_2H_5$) TABLE A (see next page).

| Cmpd. No. | Aryl | Y | Characterization |
|---|---|---|---|
| 1 | 4-Me—thien-3-yl | $CH_2OC_2H_5$ | m.p. 25–26° |
| 2 | " | $CH_2CH_2OCH_3$ | Rf = 0.45(cyclohexane/ethylacetate 1:1) |
| 3 | 2-Me—thien-3-yl | $CH_2CH_2OCH_3$ | Rf = 0.3(cyclohexane/ethylacetate 6:4) |
| 4 | 2,4-diMe—thien-3-yl | $CH_3$ | m.p. 45–46° |
| 5 | " | $C_2H_5$ | m.p. 50–51° |
| 6 | " | $iC_3H_7$ | |
| 7 | " | $CH_2$—CH=$CH_2$ | |
| 8 | " | $CH_2C(CH_3)$=$CH_2$ | m.p. 85–86° |
| 9 | " | $CH_2$—C≡CH | m.p. 95–96° |
| 10 | " | $C(CH_3)_2$—C≡CH | |
| 11 | " | $CH_2C_6H_5$ | $n_D^{20}$ = 1.5479 |
| 12 | " | $CH_2CF_3$ | m.p. 60–61° |
| 13 | " | $CH_2$—C(Cl)=$CH_2$ | |
| 14 | " | $CH_2$—C(Br)=$CH_2$ | m.p. 45–46° |
| 15 | " | $CH_2$—COOH | m.p. 145–48° |
| 16 | " | $CH_2COOMe$ | m.p. 48–49° |
| 17 | " | $CH_2COOEt$ | $n_D^{20}$ = 1.5345 |
| 18 | " | $CH_2COOC_3H_7i$ | b.p. 118–21°/0.005 Torr |
| 19 | " | $CH_2$—$COOC(CH_3)_2C$≡CH | m.p. 77–79° |
| 20 | " | $CH(CH_3)COOCH_3$ | $n_D^{20}$ = 1.5342 |
| 21 | " | $CH(CH_3)COOC_3H_7i$ | $n_D^{20}$ = 1.5192 |
| 22 | " | $CH_2CON(CH_3)_2$ | m.p. 82–84° |
| 23 | " | $CH_2CONHC_3H_7i$ | m.p. 135–137° |
| 24 | " | $CH_2CONHN$=$C(CH_3)_2$ | m.p. 141° |
| 25 | " | $CH_2$—(1-pyrazolyl) | m.p. 88–89° |
| 26 | " | $CH(CH_3)(1$-pyrazolyl) | m.p. 76–78° |
| 27 | " | $CH_2$—(3,5-diMe—pyrazolyl-1) | m.p. 143–144° |
| 28 | " | 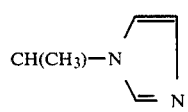 | |

-continued

| Cmpd. No. | Aryl | Y | Characterization |
|---|---|---|---|
| 29 | " | CH₂—N(imidazol-1-yl) | |
| 30 | " | CH(CH₃)—N(1,2,4-triazol-1-yl) | m.p. 132–133° |
| 31 | " | CH₂—N(1,2,4-triazol-1-yl) | |
| 32 | " | CH(Me)—N(3-methyl-2-oxo-pyrrolidin-1-yl) | |
| 33 | " | CH₂—N(2,4-dioxo-thiazolidin-3-yl) | |
| 34 | " | CH(Me)—N(3-methyl-2,4-dioxo-imidazolidin-1-yl) | |
| 35 | " | CH(Me)—N(2-oxo-oxazolidin-3-yl) | |
| 36 | " | CH₂(2-furyl) | m.p. 78–79° |
| 37 | " | CH₂—(2-thienyl) | m.p. 57–59° |
| 38 | " | CH₂—(2-methyl-thiazol-5-yl) | m.p. 66–67° |
| 39 | " | 3-Me—isoxazol-5-yl-CH₂ | m.p. 77–78° |
| 40 | " | CH₂—(5-ethyl-1,3,4-oxadiazol-2-yl) | m.p. 54–56° |
| 41 | " | CH₂—(3-methyl-1,2,4-oxadiazol-5-yl) | m.p. 71–72° |
| 42 | " | CH₂—(5-methyl-1,3,4-thiadiazol-2-yl) | m.p. 110–15° |

-continued

| Cmpd. No. | Aryl | Y | Characterization |
|---|---|---|---|
| 43 | | 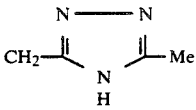 | m.p. 119–25° |
| 44 | | 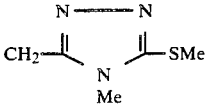 | m.p. 120–22° |
| 45 | | 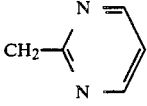 | m.p. 68–70° |
| 46 | | $CH_2CH_2OH$ | m.p. 79–80 |
| 47 | | $CH_2OEt$ | b.p. 115°/0.001 Torr |
| 48 | | $CH_2OC_3H_7n$ | $n_D^{20} = 1.5280$ |
| 49 | | $CH_2OC_4H_9n$ | b.p. 110–11°/0.001 Torr |
| 50 | | $CH(Me)OMe$ | m.p. 48–50° |
| 51 | | $CH(Et)OMe$ | m.p. 55–57° |
| 52 | | $CH_2CH_2OMe$ | m.p. 54–55° |
| 53 | | $CH_2CH_2OEt$ | b.p. 110°/0.01 Torr |
| 54 | | $CH_2CH_2OC_3H_7n$ | Rf = 0.36(diethylether/hexane 1:1) |
| 55 | | $CH(Me)CH_2OMe$ | b.p. 148–150°/0.03 Torr |
| 56 | | $C(Me)_2CH_2OMe$ | |
| 57 | | 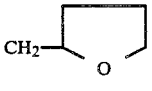 | |
| 58 | | 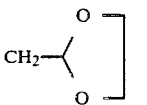 | m.p. 76–78° |
| 59 | " | $CH(Me)OCH_2CH_2Cl$ | m.p. 62–64° |
| 60 | " | $CH(OMe)CH_2OMe$ | Rf = 0.3(diethylether/hexane 1:1) |
| 61 | " | $CH_2OCH_2CH_2OMe$ | b.p. 117–18°/0.005 Torr |
| 62 | " | $CH(Me)OCH_2CH_2CN$ | m.p. 59–64° |
| 63 | " | 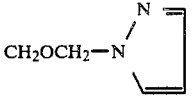 | |
| 64 | " | 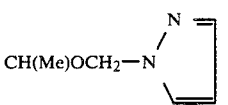 | |
| 65 | " | $CH(Me)O-N=CH-Me$ | |
| 66 | " | $CH(Me)O-N=C(Me)_2$ | |
| 67 | " | $CH_2-CH=NOMe$ | Rf = 0.31(hexane/ethylacetate 3:2) |
| 68 | " | $CH_2-CH=NOEt$ | Rf = 0.23(hexane/ethylacetate 4:1) |
| 69 | " | $CH_2-C(Me)=NOMe$ | m.p. 76–78° |
| 70 | " | $CH_2-C(Me)=NOEt$ | m.p. 57–59° |
| 71 | " | $CH(Me)CH=NOMe$ | m.p. 68–70° |
| 72 | " | $CH(Me)CH=NOEt$ | Rf = 0.4(hexane/ethylacetate 4:1) |
| 73 | " | $CH(Me)-N(Me)-COMe$ | |
| 74 | 2-Me—4-Et—thien-3-yl | $CH(Me)CH_2OMe$ | b.p. 142–44°/0.2 Torr |
| 75 | " | $CH_2OEt$ | m.p. 49–50° |
| 76 | " | pyrazolyl-1-$CH_2$ | m.p. 53–54° |
| 77 | 2-Et—4-Me—thien-3-yl | $CH_2OC_2H_5$ | Rf = 0.47(diethylether/hexane 7:3) |
| 78 | " | $CH(Me)CH_2OMe$ | Rf = 0.47(diethylether/hexane 7:3) |

-continued

| Cmpd. No. | Aryl | Y | Characterization |
|---|---|---|---|
| 79 | 2,4-diEt—thien-3-yl | pyrazolyl-1-CH$_2$ | m.p. 63–65° |
| 80 | " | CH$_2$—OEt | $n_D^{20}$ = 1.5242 |
| 81 | " | CH$_2$CH$_2$OMe | $n_D^{23}$ = 1.5328 |
| 82 | 2-iC$_3$H$_7$—4-Me—thien-3-yl | pyrazolyl-1-CH$_2$ | |
| 83 | 4-OH—2-Me—thien-3-yl | CH(Me)CH$_2$OMe | |
| 84 | 2-Me—4-MeO—thien-3-yl | pyrazolyl-1-CH$_2$ | m.p. 90–92° |
| 85 | | CH$_2$—OEt | m.p. 24° |
| 86 | | CH$_2$CH$_2$—OEt | b.p. 168–170°/0.05 Torr |
| 87 | 2-Me—4-EtO—thien-3-yl | pyrazolyl-1-CH$_2$ | |
| 88 | 2-Me—4-i-C$_3$H$_7$—thien-3-yl | " | |
| 89 | 2-Me—4-nC$_4$H$_9$O—thien- | CH$_2$OEt | m.p. 44–46° |
| 90 | 2-Me—4-OCH$_2$—CH═CH$_2$—thien-3-yl | pyrazolyl-1-CH$_2$ | |
| 91 | 2-Me—4-OCH$_2$—C≡CHthien-3-yl | " | |
| 92 | 2-MeOCH$_2$—4-MeO—thien-3-yl | " | |
| 93 | 2-MeS—4-Me—thien-3-yl | " | b.p. 180°/0.001 Torr |
| 94 | | CH$_2$OEt | b.p. 135°/0.001 Torr |
| 95 | | CH$_2$CH$_2$OMe | b.p. 148–150°/0.001 Torr |
| 96 | 2-MeS(O)—4-Me—thien-3-yl | CH$_2$OEt | m.p. 100° |
| 96a | 2-MeSO$_2$—4-Me—thien-3-yl | CH$_2$OEt | |
| 97 | 2-MeCO—4-Me—thien-3-yl | CH$_2$OEt | m.p. 37–38° |
| 97a | 2-MeCO—4-Et—thien-3-yl | pyrazolyl-1-CH$_2$ | |
| 97b | 2-MeCO—4,5-diMe—thien-3-yl | pyrazolyl-1-CH$_2$ | |
| 98 | 2-MeC(═NOMe)—4-Me—thien-3-yl | CH$_2$OEt | syn: m.p. 89–91° anti: m.p. 75–76° |
| 99 | 2-MeC(═NOMe)—4-Me—thien-3-yl | pyrazolyl-1-CH$_2$ | syn: m.p. 123° |
| 100 | 2-MeC(OEt)$_2$—4-Me—thien-3-yl | CH$_2$OEt | m.p. 46–47° |
| 101 | 2-Me—4-O—COMe—thien-3-yl | CH(Me)CH$_2$OMe | |
| 102 | 2-COOMe—4-Me—thien-3-yl | CH$_2$—C≡CH | m.p. 119–21° |
| 103 | " | CH$_2$OEt | m.p. 20–22° |
| 104 | " | CH(Me)COOEt | b.p. 135°/0.005 Torr |
| 105 | 2-iC$_3$H$_7$—4-COOMe—thien-3-yl | pyrazolyl-1-CH$_2$ | |
| 106 | 2-Et—4,5-diMe—thien-3-yl | CH$_2$OEt | $n_D^{20}$ = 1.5273 |
| 107 | " | CH$_2$COOC$_3$H$_7$i | $n_D^{20}$ = 1.5112 |
| 108 | " | pyrazolyl-1-CH$_2$ | $n_D^{20}$ = 1.5509 |
| 109 | 2,4-diMe—5-Cl—thien-3-yl | CH$_2$OEt | $n_D^{20}$ = 1.5412 |
| 110 | " | CH$_2$OCH$_2$CH$_2$OCH$_3$ | $n_D^{21}$ = 1.5321 |
| 110a | " | tetrahydrofuryl-2-CH$_2$ | Rf = 0.35(cyclohexane/ethylacetate 7:3) |
| 110b | " | iC$_3$H$_7$ | Rf = 0.38(cyclohexane/ethylacetate 6:4) |
| 111 | " | pyrazolyl-1-CH$_2$ | m.p. 68–73° |
| 112 | 2,5-diBr—4-Me—thien-3-yl | CH$_2$OEt | m.p. 75–77° |
| 113 | 2-Me—4-MeO—5-Br—thien-3-yl | pyrazolyl-1-CH$_2$ | m.p. 98–99° |
| 114 | 2,4-diMe—5-COOMe—thien-3-yl | CH$_2$OEt | b.p. 140°/0.005 Torr |
| 115 | 2,4-diMe—furan-3-yl | CH$_2$OEt | Rf = 0.5(diethylether) |
| 116 | 2,4-diMe—furan-3-yl | CH$_2$CH$_2$OMe | |
| 117 | " | CH$_2$—CH═NOMe | |
| 118 | " | CH$_2$—C(Me)═NOMe | |
| 119 | " | pyrazolyl-1-CH$_2$ | |
| 120 | 1,2,4-triMe—pyrrol-3-yl | CH$_2$—OEt | |
| 121 | " | CH$_2$CH$_2$OMe | |
| 122 | " | pyrazolyl-1-CH$_2$ | |
| 123 | " | CH$_2$—C(Me)═CH$_2$ | |
| 124 | 2-COOEt—N,3,5-tri-Mepyrrol-4-yl | pyrazolyl-1-CH$_2$ | $n_D^{24}$ = 1.5422 |
| 125 | 3,5-diMe—isoxazol-4-yl | CH(Me)COOEt | m.p. 49–50° |
| 126 | " | CH$_2$CH$_2$OMe | |
| 127 | " | CH$_2$OEt | m.p. 45–46° |
| 128 | " | pyrazolyl-1-CH$_2$ | |
| 129 | 3,5-diEt-isoxazol-4-yl | CH$_2$—C(Me)═CH$_2$ | |
| 130 | " | CH$_2$—C≡CH | b.p. 118°/0.001 Torr |
| 131 | " | CH$_2$—OEt | b.p. 107–108°/0.001 Torr $n_D^{20}$ = 1.4908 |
| 132 | 3,5-diMe—isothiazol-4-yl | CH$_2$OEt | m.p. 43–45° |
| 133 | " | CH$_2$CH$_2$OMe | |
| 134 | " | pyrazolyl-1-CH$_2$ | m.p. 109–14° |
| 135 | " | CH$_2$C≡CH | m.p. 109–12° |
| 136 | 3-Me—5-EtO—pyrazol-4-yl | CH$_2$CH$_2$OMe | m.p. 111–113° |
| 137 | 1,3,5-triMe—pyrazol-4-yl | CH$_2$OEt | b.p. 130°/0.001 Torr |
| 138 | " | CH$_2$CH$_2$OMe | m.p. 66–67° |
| 139 | " | CH$_2$—OC$_3$H$_7$n | b.p. 135°/0.001 Torr |
| 140 | " | Et | m.p. 80–82° |
| 141 | " | CH$_2$—C≡CH | m.p. 115–117° |
| 142 | " | pyrazolyl-1-CH$_2$ | m.p. 96–97° |
| 143 | 1-Me—3,5-diEt—pyrazol-4-yl | CH$_2$—OC$_3$H$_7$n | $n_D^{20}$ = 1.5008 |
| 144 | " | CH$_2$CH$_2$OMe | b.p. 130°/0.001 Torr |

-continued

| Cmpd. No. | Aryl | Y | Characterization |
|---|---|---|---|
| 145 | 1,3-diMe—5-EtO—pyrazol-4-yl | CH$_2$OEt | m.p. 54–56° |

INTERMEDIATES

EXAMPLE 8

Methyl 3,5-dimethyl-4-amino-thiophene-2-carboxylate

A solution of 45.2 g (0.21 mol) methyl 3,5-dimethyl-4-nitrothiophene-2-carboxylate in 1000 ml methanol is hydrogenated for two hours at 10 bar in the presence of 4.5 g palladium (10% on carbon).

When the reduction is completed the mixture is filtered, the catalyst washed with methanol and the filtrate evaporated to dryness.

The crystalline residue is treated with diethyl ether, yielding the analytically pure title compound m.p. 88°–89°.

EXAMPLE 9

2,4-Dimethyl-3-aminothiophene

To 890 ml (3 mol) of sodium bis(2-methoxyethoxy)aluminium hydride (70% solution in toluene) and 600 ml of dry toluene is added, dropwise with vigorous stirring, a solution of 100 g (0.58 mol) of methyl 3-amino-4-methylthiophene-2-carboxylate in 700 ml of dry toluene at such a rate that the temperature does not rise above 55°.

After the addition is completed stirring is continued for a further 30 minutes and the reaction mixture then cautiously added in small portions at 0° to 1200 ml of 20% potassium hydroxide solution.

The toluene layer is separated, dried over MgSO$_4$ and evaporated in vacuo. The residual brown liquid is distilled under diminished pressure, affording the analytically pure title compound, b.p. 49°–52°/0.01 Torr.

EXAMPLE 10

4-Methoxy-2-methyl-3-amino-thiophene

The well stirred mixture of 55.4 g (0.2 mol) of benzyl N-(4-methoxy-2-methyl-thien-3-yl)carbamate, 40 g (0.7 mol) of KOH, 600 ml of ethanol and 120 ml of water is heated under reflux for two hours. The resulting solution is then evaporated in vacuo and the residue diluted with 500 ml of water. The separating light yellow oil is taken up in 400 ml of diethyl ether and the aqueous phase extracted once with 400 ml of ether.

The combined ethereal solutions are dried (Na$_2$SO$_4$) and filtered. A slow current of dry hydrogen chloride is then passed through the filtrate for a period of 30 minutes, taking care—by intermittent colling in an ice bath—that the temperature does not rise above 10°.

The precipitated hydrochloride of the title compound has a m.p. of 230° (the free base a m.p. of 61°–63°).

EXAMPLE 11

2-Methylthio-4-methyl-3-aminothiophene 6 g (0.22 gram atoms) freshly prepared aluminium amalgam are added over a period of about two minutes to 18.9 g (0.1 mol) of 2-methylthio-4-methyl-3-nitrothiophene dissolved in 200 ml of moist diethylether. The vigorous reaction which sets in after 5–10 minutes is kept under control by cooling the flask in ice.

After 45 minutes, when the exothermic reaction has subsided and all the aluminium has reacted, another six grams of amalgamated aluminium are added.

The reaction mixture is then gently refluxed for 2 hours; during this period the formation of the thiophene amine is complete. The organic phase is decanted and the remainder washed with two 50 ml portions of diethylether. The combined ethereal solutions are dried (MgSO$_4$) and evaporated in vacuo. The residual crude title compound is distilled under reduced pressure, having a boiling point of 79°–81°/0.5 Torr.

EXAMPLE 12

In the following table are listed compounds of formula IX that are obtained according to one or more of the procedures of Examples 8 to 11.

| | |
|---|---|
| Ex. 12.1 | 1,3-di-CH$_3$—5-OC$_2$H$_5$—4-NH$_2$pyrazole (Rf = 0.28 tetrahydrofurane:hexane 9:1) |
| Ex. 12.2 | 3,5-di-CH$_3$—4-NH$_2$—isothiazole (m.p. 82–84°) |
| Ex. 12.3 | 4-C$_2$H$_5$—2-CH$_3$—3-aminothiophene, Rf = 0.25 (diethylether:hexane 2:1) |
| Ex. 12.4 | 4-n-butoxy-2-methyl-3-amino-thiophene, m.p. 25°; (Rf = 0.25 (diethylether/hexane 2:1) |
| Ex. 12.5 | 5-C$_2$H$_5$O—3-CH$_3$—4-NH$_2$—pyrazole m.p. 81–83° |
| Ex. 12.6 | 3,5-di-C$_2$H$_5$—1-CH$_3$—4-NH$_2$—pyrazole b.p. 68–70°/0.001 Torr |
| Ex. 12.7 | 3,5-di-C$_2$H$_5$—4-NH$_2$—isoxazole Rf = 0.39 (diethyl ether) |
| Ex. 12.8 | (3-NH$_2$—4-Me—thien-2-yl)ethanone, m.p. 80–81° |
| Ex. 12.9 | (3-NH$_2$—4-Et—thien-2-yl)ethanone, m.p. 68° |
| Ex. 12.10 | (3-NH$_2$—4,5-diMe—thien-2-yl)ethanone, m.p. 120–23° |
| Ex. 12.11 | 2-Et—4-Me—3-NH$_2$—thiophene, b.p. 74–76°/0.01 Torr |
| Ex. 12.12 | 2,4-diEt—3-NH$_2$—thiophene, Rf = 0.24 (CH$_2$Cl$_2$) n$_D^{20}$ = 1.5511 |
| Ex. 12.13 | 2-Et—4,5-diMe—3-NH$_2$—thiophene, n$_D^{20}$ = 1.5581 |

EXAMPLE 13

N-(2,4-dimethyl-thien-3-yl)-acetoxyacetamide

To 12.7 g (0.1 mol) of 2,4-dimethyl-3-aminothiophene, 13.8 g (0.1 mol) of K$_2$CO$_3$, 20 ml of water and 150 ml of methylene chloride are added dropwise at ambient temperature 15 g (0.11 mol) of acetoxyacetyl chloride.

After the exothermic reaction has subsided, stirring is continued for a further hour. Then the organic layer is evaporated, washed with water, dried (MgSO$_4$) and evaporated in vacuo. The solid residue is treated with hexane affording the analytically pure title compound, m.p. 110°–112°.

EXAMPLE 14

N-(2,4-dimethyl-thien-3-yl)-hydroxyacetamide

Through a stirred solution of 15.9 g (0.07 mol) of N-(2,4-dimethyl-thien-3yl)-acetoxyacetamide in 300 ml of methanol is bubbled a gentle stream of ammonia gas for 30 minutes.

After the exothermic (40°) reaction (moderated by intermittent cooling in cold water) has subsided, stirring is continued for additional 30 minutes and the reaction solution then evaporated to dryness. The resulting solid is recrystallized from ethylacetate, giving the analytically pure title compound as colourless crystals, m.p. 85°–87°.

EXAMPLE 15

N-(2-ethoxyethyl)-4-methoxy-2-methyl-thiophene-3-amine

To 70 ml (0.245 mol) of sodium bis(2-methoxyethoxy)aluminium hydride (70% solution in toluene) and 30 ml of dry toluene is added dropwise with stirring a solution of 9.4 g (0.041 mol) of N-(4-methoxy-2-methyl-thien-3-yl)-ethoxyacetamide in 125 ml of dry toluene. After the exothermic reaction has subsided, stirring is continued for a further 90 minutes and the reaction solution then cautiously added in small portions at −10° to 100 ml of 20% KOH solution.

The toluene layer is separated and the aqueous phase extracted twice with 100 ml of toluene. The combined toluene solutions are dried ($Na_2SO_4$) and evaporated in vacuo. The residual light brown liquid is analytically pure, Rf=0.32 (hexane-diethyl ether 1:2).

EXAMPLE 16

N-[(Methoxymethyl)ethyl]-2,4-dimethyl-thiophene-3-amine

The solution of 6.4 g (0.05 mol) of 2,4-dimethyl-3-amino-thiophene and 5,3 g (0.06 mol) of methoxyacetone in 100 ml of dry toluene is boiled under reflux until the theoretical amount of water has separated in the water trap (2½ hours). The toluene solution is then allowed to cool to ambient temperature and evaporated in vacuo. The residual crude Schiff base is sufficiently pure for the next step.

9.2 g (0.048 mol) of this material are dissolved in 100 ml of dry toluene and added without cooling to a well stirred solution of 28 ml (0.098 mol) of sodium bis(2-methoxyethoxy)aluminium hydride (70% solution in toluene) in 15 ml of dry toluene.

After the exothermic reaction (44°) has subsided, stirring is continued for a further 90 minutes and the brown reaction solution then cautiously added in small portions at −10° to 40 ml of 20% KOH solution.

The toluene layer is then separated, dried ($Na_2SO_4$) and evaporated in vacuo. The residual oil, after column chromatography on silica gel (elution with hexane-diethyl ether 3:1) is distilled under diminished pressure (ball tube), having a b.p. of 94°–95°/0.01 Torr.

EXAMPLE 17

N-(5-Ethyl-1,3,4-oxdiazol-2-ylmethyl)-2,4-dimethylthiophene-3-amine

The mixture of 12.7 g (0.1 mol) of 2,4-dimethyl-3-amino-thiophene, 14.6 g (0.1 mol) of 2-chloromethyl-5-ethyl-1,3,4-oxdiazole and 13.8 g (0.1 mol) of $K_2CO_3$ in 150 ml of dry dimethylformamide (=DMF) is stirred for 20 hours at 80°.

The reaction mixture is then cooled to ambient temperature poured into 400 ml of water and the water-DMF solution extracted with three 150 ml portions of diethyl ether. The combined ethereal extracts are dried over anhydrous $Na_2SO_4$ and evaporated in vacuo. The residual brown oil is chromatographed on a silica gel column, elution with hexane/diethyl ether 1:1 affords the title compound as an analytically pure orange liquid, Rf=0.2 (ether-hexane 1:1).

EXAMPLE 18

N-(2,4-dimethyl-thien-3-yl)glycine hydrazide 82 g (0.412 mol) N-(2,4-dimethyl-thien-3-yl)glycine-methylester and 42 g (1.3 mol) hydrazine hydrate in 350 ml alcohol are stirred for 24 hours at room temperature. The mixture is evaporated in vacuo. After adding 150 ml water the residue is treated with 4×500 ml portions of ether. The ether phase is dried over $Na_2SO_4$ and evaporated to dryness giving the analytically pure title compound, m.p. 68°–70° C.

EXAMPLE 19

N-(2,4-dimethyl-thien-3-yl)-N-(4-methyl-5-mercapto-1,2,4-triazol-3-yl-methyl)-amine A mixture of 15 g (0.075 mol) N-(2,4-dimethyl-thien-3yl)glycine hydrazide and 5.5 g (0.075 mol) methylisothiocyanate in 100 ml ethanol is refluxed for 4 hours. The reaction mixture is cooled to 6° C. and the precipitate formed separated by filtration giving the pure compound, m.p. 184°–87°C.

EXAMPLE 20

N-(2,4-dimethyl-thien-3-yl)-N-(4-methyl-5-methylmercapto-1,2,4-triazol-3-yl-methyl)-amine To a mixture of 9.5 g (0.037 mol) N-(2,4-dimethyl-thien-3-yl)-N-(4-methyl-5-mercapto-1,2,4-triazol-3-yl-methyl)-amine, 1.1 g triethyl-benzyl ammonium chloride in 100 ml toluene and 30 ml aqueous 50% sodium hydroxide solution are added 4.7 g (0.037 mol) dimethylsulfate. The reaction mixture is stirred at room temperature for 5 hours, the organic layer is separated, washed with three 100 ml portions of water, dried over $Na_2SO_4$ and evaporated to dryness. The residue is recrystallized twice from ether giving the pure title compound, m.p. 92°–96° C.

EXAMPLE 21

N-(2,4-dimethyl-thien-3-yl)-N-(5-methyl-1,3,4-thiadiazol-2-yl-methyl)-amine

To 10 g (0.05 mol) N-(2,4-dimethyl-thien-3-yl)-glycine hydrazide in 175 ml methylene chloride is added dropwise 5.5 g (0.05 mol) acetic acid anhydride. The mixture is stirred for 1 hour at 20° C. and evaporated to dryness. The oily residue is dissolved in 150 ml pyridine and 11.1 g (0.05 mol) phosphorous pentasulfide is added in small portions. During the course of the addition the temperature reached 48° C. The mixture is refluxed for two hours and stirred at room temperature for another 16 hours. After evaporation to dryness the residue is dissolved in methylene chloride and the solution treated successively with ice water, diluted cold sodium hydroxide solution and water, dried over $Na_2SO_4$ and evaporated to dryness. Chromatography on a silica gel column afforded the pure compound as an oil, Rf=0.23 (ethylacetate/hexane 6:4).

EXAMPLE 22

N-(2,4-dimethyl-thien-3-yl)-N-5-methyl-1,2,4-triazol-3-yl-methyl)amine

To a stirred solution of 2.2 g (0.055 mol) NaOH in 125 ml methanol is added 5 g (0.05 mol) acetamidine hydrochloride. After 15 minutes 10 g (0.05 mol) N-(2,4- dimethyl-thien-3-yl)-glycine hydrazide is added and the mixture refluxed for 18 hours. After evaporation to dryness the residue is treated with methylene chloride and freed from insoluble by-products by filtration. Evaporation of the methylene chloride gives the title compound, m.p. 85°–87° C.

EXAMPLE 23

N-(2,4-dimethyl-thien-3-yl)glycine-isopropylidenehydrazide 7 g (0.035 mol) N-(2,4-dimethyl-thien-3-yl)-glycine hydrazide in 50 ml acetone is stirred at room temperature for 2 hours. The pure title compound which crystallized was obtained by filtration, m.p. 126°–28° C.

EXAMPLE 24

The following compounds of formula VII are obtained according to one or more of the preceding Examples 13 to 23:

EXAMPLE 25

N-(2-carbomethoxy-3,5-dimethyl-thien-4-yl)-chloroacetamide

To 12.25 g (0.066 mol) of methyl 3,5-dimethyl-4-aminothiophene-2-carboxylate, 9.1 g (0.066 mol) of $K_2CO_3$, 25 ml of water and 150 ml of methylene chloride are added without cooling 7.5 g (0.066 mol) of chloroacetyl chloride.

After the exothermic reaction (36°) has subsided stirring is continued for a further hour. Then the organic layer is separated, washed with water and dried over anhydrous $Na_2SO_4$. After removal of the solvent the desired product is obtained as colourless crystals, m.p. 157°–58°.

| Ex. | Ar | Y | Characterization |
|---|---|---|---|
| 24.1 | 2,4-di-$CH_3$—thien-3-yl | $CH_2CH_2$—$OCH_3$ | Rf = 0.32(diethyl ether-hexane 3:1) |
| 24.2 | 2,4-di-$CH_3$—thien-3-yl | $C_2H_5$ | Rf = 0.23(diethyl ether-hexane 1:1) |
| 24.3 | 2,4-di-$CH_3$—thien-3-yl | $CH_2$-(thienyl) | Rf = 0.38(diethyl ether-hexane 1:1) |
| 24.4 | 2,4-di-$CH_3$—thien-3-yl | $CH_2$-(furyl) | Rf = 0.39(diethyl ether-hexane 2:1) |
| 24.5 | 2-$CH_3$S—4-$CH_3$—thien-3-yl | $CH_2CH_2$—$OCH_3$ | b.p. 86°/0.01 Torr |
| 24.6 | 1,3,5-tri-$CH_3$—pyrazol-4-yl | $CH_2CH_2$—$OCH_3$ | b.p. 92–94°/0.01 Torr |
| 24.7 | 1-$CH_3$—3,5-di-$C_2H_5$—pyrazol-4-yl | $CH_2CH_2$—$OCH_3$ | Rf = 0.38(acetone-hexane 4:6) |
| 24.8 | 1,3,5-tri-$CH_3$—pyrazol-4-yl | $C_2H_5$ | Rf = 0.2(ethyl-acetate-$CH_3OH$ 2:1) |
| 24.9 | 3-$CH_3$—5-$OC_2H_5$—pyrazol-4-yl | $CH_2CH_2OCH_3$ | Rf = 0.25(ethyl-acetate-$CH_3OH$ 9:1) |
| 24.10 | 2,4-di-$CH_3$—thien-3-yl | $CH_2CH_2OC_2H_5$ | Rf = 0.48(diethyl ether) |
| 24.11 | 2,4-di-$CH_3$—thien-3-yl | $CH_2CH_2OC_3H_7$—n | Rf = 0.57(diethyl ether) |
| 24.12 | 2,4-di-$CH_3$—thien-3-yl | $CH_2CF_3$ | $n_D^{20}$ = 1.4786 |
| 24.13 | 2,4-di-$C_2H_5$—thien-3-yl | $CH_2CH_2OCH_3$ | $n_D^{20}$ = 1.5238 |
| 24.14 | 2-$CH_3$—4-$C_2H_5$—thien-3-yl | CH($CH_3$)—$CH_2OCH_3$ | b.p. 98–100°/0.09 Torr |
| 24.15 | 2-$C_2H_5$—4-$CH_3$—thien-3-yl | CH($CH_3$)—$CH_2OCH_3$ | Rf = 0.52(ether-hexane 7:3) |
| 24.16 | 2,4-di-$CH_3$—thien-3-yl | $CH_2$—C($CH_3$)=$CH_2$ | Rf = 0.55(diethylether-hexane 1:1) |
| 24.17 | 2,4-di-$CH_3$—thien-3-yl | $CH_2$-(pyrimidinyl) | |
| 24.18 | 2,4-di-$CH_3$—thien-3-yl | $CH_2$-(methylthiazolyl) | |
| 24.19 | 2,4-di-$CH_3$—thien-3-yl | $CH_2$-(oxadiazolyl) | Rf = 0.15($CH_2Cl_2$) |
| 24.20 | 2,4-di-$CH_3$—thien-3-yl | $CH_2CON(CH_3)_2$ | $n_D^{20}$ = 1.5579 |
| 24.21 | 2,4-di-$CH_3$—thien-3-yl | $CH_2COOCH_3$ | b.p. 82–87°/0.005 Torr |

EXAMPLE 26

N-(2-chloro-3,5-dimethyl-thien-4-yl)-chloroacetamide

To the stirred solution of 5.0 g (0.0245 mol) of N-(2,4-dimethylthien-3-yl)-chloroacetamide in 50 ml of dry $CH_2Cl_2$ are added dropwise at 0° 3.3 g (0.0245 mol) of sulfuryl chloride.

When the addition is complete, the reaction mixture is allowed to warm to ambient temperature and stirred for a further period of 20 hours. Then the solvent is removed in vacuo and the crystalline residue triturated with hexane, yielding the analytically pure title compound, m.p. 166°, decomp.

EXAMPLE 27

N-[2-(1,1-diethoxy)ethyl-4-methyl-thien-3-yl]-chloroacetamide 15 g (0.065 mol) of N-(2-acetyl-4-methyl-thien-3-yl)-chloroacetamide are dissolved in the warm (50°) mixture of 60 g of dry ethyl alcohol, 60 g of triethyl orthoformate and 7 drops of concentrated HCl.

Upon standing for 30 hours at room temperature the reaction mixture is evaporated in vacuo (50°/0.01 Torr) and the residual brown syrup chromatographed on a silica gel column. Elution with hexane-diethylether 2:1 affords the title compound as colourless crystals, having a m.p. of 57°–58°.

EXAMPLE 28

N-[2-(1-methoxyimino)ethyl-4-methyl-thien-3-yl]-chloroacetamide

The solution of 1.5 g (0.0065 mol) of N-(2-acetyl-4-methyl-thien-3-yl)-chloroacetamide and 6.6 g (0.14 mol) of methoxyamine in 50 ml of dry toluene, which contains 5 g of molecular sieves (3 Å) is refluxed for 7 hours.

The yellow reaction solution is then filtered and evaporated in vacuo. The resulting crude syn/anti isomer mixture is separated by chromatography with hexane-diethylether as the mobile phase.

First are eluted 0.6 g of the pure isomer (syn isomer) with the m.p. of 101°–102° (Rf=0.33, hexane-ether 1:1). Continued elution of the silica gel column affords the other analytically pure anti isomer (0.4 g) having a melting point of 87°–89° (Rf=0.21).

EXAMPLE 29

The following compounds of formula III are obtained according to one or more of the Examples 25 to 28:

| Ex. | Ar | Characterization |
|---|---|---|
| 29.1 | 2-COOCH$_3$—4-CH$_3$—thien-3-yl | m.p. 118–119° |
| 29.2 | 2-CH$_3$S—4-CH$_3$—thien-3-yl | m.p. 105–106° |
| 29.3 | 2,4-di-CH$_3$—thien-3-yl | m.p. 128–129° |
| 29.4 | 3,5-di-CH$_3$—isoxazol-4-yl | m.p. 96–98° |
| 29.5 | 3,5-diC$_2$H$_5$—isoxazol-4-yl | m.p. 67–69° |
| 29.6 | 4-CH$_3$—thien-3-yl | m.p. 93–96° |
| 29.7 | 2-CH$_3$—4-C$_2$H$_5$—thien-3-yl | m.p. 114° |
| 29.8 | 2-CH$_3$—4-OCH$_3$—thien-3-yl | m.p. 144–45° |
| 29.9 | 2,4-di-CH$_3$—furan-3-yl | m.p. 95–97° |
| 29.10 | 3,5-di-CH$_3$—isothiazol-4-yl | m.p. 104–06° |
| 29.11 | 3-CH$_3$—5-OC$_2$H$_5$—pyrazol-4-yl | m.p. 125–27° |
| 29.12 | 2-COOC$_2$H$_5$—N,3,5-tri-CH$_3$—pyrrol-4-yl | m.p. 163–65° |
| 29.13 | 2-C$_2$H$_5$—4-CH$_3$—thien-3-yl | m.p. 105° |
| 29.14 | 2,4-di-C$_2$H$_5$—thien-3-yl | m.p. 145° |
| 29.15 | 2-COCH$_3$—4-CH$_3$—thien-3-yl | m.p. 110° |
| 29.16 | 2-CH$_3$—4-OC$_4$H$_9$n-thien-3-yl | m.p. 129–30° |
| 29.17 | 2-C$_2$H$_5$—4,5-diCH$_3$—thien-3-yl | m.p. 147–48° |

EXAMPLE 30

N-(2,4-dimethylthien-3-yl)-N-methoxyethyl-hydroxyacetamide 18.4 g (0.1 mol) of N-(2,4-dimethylthien-3-yl)-hydroxyacetamide in 50 ml of dry dimethylformamide (=DMF) are added dropwise to a well stirred suspension of 3.0 g (0.1 mol) of sodium hydroxide (80% dispersion in mineral oil) in 50 ml of dry DMF.

After the exothermic reaction (50°) has subsided, the solution of the Na-salt is allowed to reach room temperature and then treated with the solution of 10.4 g (0.11 mol) of 2-chloroethylmethylether in 20 ml of dry DMF. When the addition is completed, the resulting mixture is heated at 100° for 4 hours and then evaporated to dryness (40°/0.1 Torr).

The residue is taken up with 200 ml of diethyl ether, washed with 250 ml of water, dried (MgSO$_4$) and filtered. The residual oil left on evaporing the filtrate is chromatographed on a silica gel column. Elution with ether affords the desired product as an analytically pure viscous liquid (Rf=0.25/ether).

EXAMPLE 31

Following the procedure of Example 30, the following compounds of formula II, in which Ar is 2,4-dimethylthien-3-yl, are obtained.

| Ex. | Y | Characterization |
|---|---|---|
| 31.1 | CH$_2$CH=NOCH$_3$ | Rf = 0.21(hexane-ethyl-acetate 3:2) |
| 31.2 | CH$_2$CH=NOC$_2$H$_5$ | Rf = 0.25(hexane-ethyl-acetate 3:2) |
| 31.3 | CH$_2$C=NOCH$_3$<br>    │<br>    CH$_3$ | m.p. 69–71° |
| 31.4 | CH$_2$—C=NOC$_2$H$_5$<br>       │<br>       CH$_3$ | Rf = 0.27(hexane-ethyl-acetate 3:2) |
| 31.5 | CHCH=NOCH$_3$<br>│<br>CH$_3$ | Rf = 0.31(hexane-ethyl-acetate 3:2) |
| 31.6 | CHCH=NOC$_2$H$_5$<br>│<br>CH$_3$ | Rf = 0.3(hexane-ethyl-acetate 3:2) |
| 31.7 | 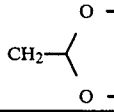 | Rf = 0.12(hexane-ethyl-acetate 3:2) |

EXAMPLE 32

N-(4-Methoxy-2-methyl-thien-3-yl)ethoxyacetamide

To 9.8 g (0.068 mol) 4-methoxy-2-methyl-3-aminothiophene, 9.45 g (0.068 mol) K$_2$CO$_3$, 35 ml of water and 100 ml of CH$_2$Cl$_2$ is added without cooling the solution of 8.4 g (0.069 mol) of ethoxyacetyl chloride in 20 ml of CH$_2$Cl$_2$.

After the exothermic reaction (32°) has subsided, stirring is continued for a further hour. Then the organic layer is separated, washed twice with 150 ml of water and dried over anhydrous $Na_2SO_4$.

The residue left on rotevaporation of the solvent is subjected to column chromatography on silica gel. Elution with hexane-diethylether 1:1 affords the analytically pure title compound having a m.p. of 40°–41°.

EXAMPLE 33

Analogous to the procedure of Example 34, the following amides of formula $ArNHCOY_3$ are obtained.

| Ex. | Ar | $Y_3$ | Characterization |
|---|---|---|---|
| 33.1 | 2,4-di-$CH_3$—thien-3-yl | —$CH_2$—$OCH_3$ | m.p. 62–63° |
| 33.2 | 2,4-di-$CH_3$—thien-3-yl | —$CH_3$ | m.p. 168–69° |
| 33.3 | 2,4-di-$CH_3$—thien-3-yl | 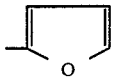 | m.p. 140–42° |
| 33.4 | 2,4-di-$CH_3$—thien-3-yl | 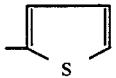 | m.p. 164–65° |
| 33.5 | 1,3,5-tri-$CH_3$—pyrazol-4-yl | —$CH_2OCH_3$ | m.p. 85–87° |
| 33.6 | 1-$CH_3$—3,5-di-$C_2H_5$—pyrazol-4-yl | —$CH_2OCH_3$ | b.p. 120°/ 0.001 Torr |
| 33.7 | 3-$CH_3$—5-$OC_2H_5$—pyrazol-4-yl | —$CH_2OCH_3$ | m.p. 128–30° |
| 33.8 | 2,4-di-$CH_3$—thien-3-yl | —$CH_2OC_2H_5$ | m.p. 37–38° |
| 33.9 | 2,4-di-$CH_3$—thien-3-yl | —$CH_2OC_3H_7$—n | m.p. 43–45° |
| 33.10 | 2,4-di-$CH_3$—thien-3-yl | $CF_3$ | m.p. 94–97° |
| 33.11 | 2,4-di-$C_2H_5$—thien-3-yl | —$CH_2OCH_3$ | m.p. 48–49° |

EXAMPLE 34

Benzyl(N-4-methoxy-2-methyl-thien-3-yl)carbamate 63.6 g (0.23 mol) of diphenylphosphoryl azide and 24.4 g (0.23 mol) of triethylamine are added all at once to the stirred suspension of 36.5 g (0.21 mol) of 4-methoxy-2-methyl-thiophene-3-carboxylic acid in 300 ml of dry benzene.

The resulting mixture is refluxed for one hour and then treated with 25 g (0.23 mol) of benzyl alcohol.

After a reaction period of 3½ hours at 78° the reaction mixture is cooled to ambient temperature, diluted with diethyl ether (350 ml) and washed successively with 250 ml of 5% HCl, 250 ml of saturated $NaHCO_3$ solution and 200 ml of saturated NaCl solution. The crystalline residue left on rotevaporation of the dried ($Na_2SO_4$) solvent is triturated with pentane, yielding the analytically pure title compound, m.p. 107°–108°.

EXAMPLE 35

Following the procedure of Example 34, employing the appropriate carboxylic acid, the following carbamate is obtained.

Ex. 35.1: Benzyl(N-2,4-di-$CH_3$-furan-3-yl)carbamate, m.p. 103°–5°.

Ex. 35.2: Benzyl(N-4-n-butoxy-2-methyl-thien-3-yl)carbamate, m.p. 83°.

EXAMPLE 36

4-Methoxy-2-methyl-thiophene-3-carboxylic acid

The title compound is obtained by saponification (KOH) of the corresponding ethyl ester; m.p. 127°.

EXAMPLE 37

Analogous to the procedure of Example 36 is obtained 4-n-butoxy-2-methyl-thiophene-3-carboxylic acid, m.p. 66°–68°.

EXAMPLE 38

Ethyl 4-methoxy-2-methyl-thiophene-3-carboxylate 20 ml of 50% sodium hydroxide solution are added dropwise to a mixture of 18.6 g (0.1 mol) of ethyl 4-hydroxy-2-methyl-thiophene-3-carboxylate, 10 ml (0.105 mol) of dimethyl sulphate and 2.3 g (0.01 mol) of benzyltriethylammonium chloride in 100 ml of $CH_2Cl_2$, at ambient temperature.

After about 15 minutes of reflux, the reaction mixture is worked up to give the title compound, Rf=0.36 (diethyl ether:hexane 2:1).

EXAMPLE 39

Methyl 3,5-dimethyl-4-nitrothiophene-2-carboxylate

To a well stirred, chilled (0°) solution of 51.4 g (0.3 mol) of methyl 3,5-dimethylthiophene-2-carboxylate in 200 ml of glacial acetic acid are added dropwise over a period of 40 minutes, a mixture of 30 ml of fuming nitric acid (specific gravity=1.5) and 120 ml of acetic anhydride. After the addition is completed the resulting brown solution is stirred a further two hours at 5° and then poured into 3000 ml of ice water.

The aqueous phase is extracted twice with 500 ml of diethyl ether. The ethereal extracts are washed with water and 3% sodium bicarbonate solution, dried ($Na_2SO_4$) and evaporated in vacuo.

The residue is subjected to column chromatography on silica gel. Elution with hexane-diethylether (10:1) afforded the title compound having a melting point of 87°–88°.

EXAMPLE 40

Analogous to the process of Example 39 but employing 1,3-dimethyl-5-ethoxypyrazole as starting material is obtained 1,3-dimethyl-5-ethoxy-4-nitropyrazole; Rf=0.37 with diethylether on silica gel.

HERBICIDAL TESTS

EXAMPLE 41

Weed Control—Pre-emergence treatment

Seed pots (7 cm diameter) are filled with a mixture of peat culture substrate and sand. The exposed surface of the peat culture substrate and sand mixture is sprayed with a test liquid of a test compound (e.g. formulated in accordance with Example B) and seeds of *Lepidium sativum, Agrostis alba, Avena sativa* and *Lolium perenne* are sown in each pot, whereby the *Avena sativa* and *Lolium perenne* seeds are, after sowing covered with a thin layer (0.5 cm) of peat culture substrate/sand mixture. The pots are kept for 21 days at room temperature with 14 to 17 hours light (daylight or its equivalent) per day.

Determination of the herbicidal effect of the particular herbicide is made after the 21 day period. The determination involves a visual evaluation of the degree and quality of damage to the various seed plants.

The compounds of formula I are applied in the above manner at dosages equivalent to 1.4 and 5.6 kg of active agent/hectare.

Herbicidal activity, that is to say, significant damage to the test plants is observed.

EXAMPLE 42

Weed Control—Post-emergence treatment

A procedure similar to that employed in Example 41 is followed with the exception that the test compounds (herbicides) are applied when the plants are at the 2-4 leaf stage, the sowing of the plant seeds being staggered to ensure that the plants reach the 2-4 leaf stage at about the same time.

Again the compounds of formula I are applied in the above manner at dosages corresponding to 1.4 kg/ha and 5.6 kg/ha. The determination of the herbicidal effect is made 21 days after application of the test compounds and involves an analogous evaluation as described in Example 41. Herbicidal activity is observed.

EXAMPLE 43

Representative compounds of the invention are evaluated in the following pre-emergence test procedure.

Seed dishes measuring 30×40 cm are filled to a depth of 6 cm with a mixture of peat culture substrate and sand. The exposed surface of the peat culture substrate and sand mixture is sprayed with an aqueous test liquid (e.g. formulated in accordance with Example B) comprising a compound of the invention in a given concentration. The spray volume corresponds to 600 l aqueous test liquid/ha. The same test is repeated with various concentrations of test liquid, whereby the concentrations are selected in such a manner that the desired application rates are realized. Six species of seed are then sown in each dish. The number of seeds sown for each plant species depends on the seed germination potential and also the initial growth size of the particular seed plant. After sowing of the seeds, the treated surface is covered with a thin layer about 0.5 cm deep of the peat culture substrate and sand mixture.

The prepared seed dishes are kept for 28 days at a temperature of 20° to 24° C. and 14 to 17 hours light each day.

Determination of the herbicidal effect of the particular compound of the invention is made after the 28 day period. The determination involves a visual evaluation of the degree and quality of damage to the various plants. Particular advantageous herbicidal properties are i.a. observed with the Compound Nos. 25, 26, 47, 48, 55, 75, 84 and 86 of Table A. Some of the results obtained with an application rate corresponding to 1 kg active ingredient/hectare are summarised in the following Table B.

EXAMPLE 44

Post-emergence Treatment

A further evaluation of representative compounds of the formula I is effected in a post-emergence test procedure similar to that of the pre-emergence test described in Example 43, except that the herbicide test liquid is applied when the plants are at a 2-4 leaf stage. For that purpose the various plants species are sown in time-staggered relationship. The greenhouse conditions (temperature, light) are as in Example 43. Determination of the herbicidal effect is also effected 28 days after application according to the method of Example 41.

Particular advantageous herbicidal properties are i.a. observed with the Compound Nos. 25, 26, 47, 48, 55, 75, 84 and 86 of Table A. Some of the results obtained with application rates corresponding to 5 kg active ingredient/hectare are summarised in the following Table C.

TABLE B

| Plant treated | Pre-emergence application 1 kg/ha Compound Tested - % damage | | | | | | | |
|---|---|---|---|---|---|---|---|---|
| | 25 | 26 | 47 | 48 | 55 | 75 | 84 | 86 |
| Amaran. retrofl. | 90 | 90 | 100 | 100 | 100 | 100 | 80 | 90 |
| Capsella b.p. | 80 | 100 | 100 | 80 | 90 | 70 | 70 | 90 |
| Chenop. alb. | 80 | 80 | 90 | 50 | 20 | 50 | 60 | 60 |
| Galium aparine | 80 | 10 | 50 | 0 | 10 | 10 | 50 | 10 |
| Senecio vulg. | 90 | 80 | 80 | 80 | 80 | 100 | 90 | 100 |
| Stellaria media | 90 | 70 | 70 | 80 | 50 | 50 | 70 | 90 |
| Alfalfa | 80 | 60 | 60 | 50 | 80 | 10 | 70 | 90 |
| Bean | 0 | 0 | 20 | 20 | 0 | 0 | 10 | 10 |
| Carrot | 80 | 90 | 90 | 90 | 70 | 100 | 80 | 90 |
| Cotton | 20 | 0 | 10 | 0 | 0 | 0 | 20 | 0 |
| Flax | 80 | 30 | 60 | 50 | 30 | 0 | 20 | 10 |
| Potato | 0 | 10 | 10 | 0 | 0 | 0 | 0 | 0 |
| Soya | 50 | 10 | 30 | 30 | 0 | 10 | 30 | 30 |
| Sugar beet | 60 | 10 | 10 | 0 | 0 | 0 | 20 | 30 |
| Rape | 10 | 0 | 20 | 0 | 0 | 0 | 20 | 10 |
| Sunflower | 0 | 10 | 30 | 50 | 0 | 0 | 0 | 10 |
| Agropyron repens | 90 | 100 | 90 | 60 | 80 | 90 | 90 | 70 |
| Agrostis alba | 100 | 100 | 100 | 100 | 100 | 100 | 100 | 100 |
| Alopec. myos. | 90 | 90 | 80 | 20 | 50 | 80 | 80 | 90 |
| Apera sp. venti. | 100 | 100 | 100 | 100 | 100 | 100 | 100 | 100 |
| Avena fatua | 80 | 80 | 80 | 40 | 80 | 90 | 50 | 90 |
| Echinochloa c.g. | 90 | 100 | 90 | 90 | 90 | 100 | 90 | 90 |
| Corn | 20 | 30 | 50 | 30 | 0 | 50 | 90 | 60 |
| Wheat | 70 | 100 | 90 | 90 | 0 | 100 | 60 | 70 |

TABLE C

| Plant treated | Post-emergence application 5 kg/ha Compound Tested - % damage | | | | | | | |
|---|---|---|---|---|---|---|---|---|
| | 25 | 26 | 47 | 48 | 55* | 75 | 84 | 86* |
| Amaran. retrofl. | 90 | 80 | 70 | 50 | 80 | 60 | 80 | 90 |
| Capsella b.p. | 80 | 60 | 20 | 20 | 80 | 50 | 80 | 60 |
| Chenop. alb. | 90 | 40 | 40 | 20 | 20 | 40 | 30 | 60 |
| Galium aparine | 80 | 60 | 40 | 30 | 80 | 20 | 70 | 60 |
| Senecio vulg. | 80 | 50 | 70 | 80 | 90 | 90 | 80 | 90 |
| Stellaria media | 90 | 50 | 60 | 10 | 30 | 40 | 60 | 40 |
| Alfalfa | 80 | 60 | 20 | 10 | 50 | 20 | 70 | 70 |
| Bean | 100 | 20 | 30 | 20 | 20 | 30 | 30 | 50 |
| Carrot | 70 | 90 | 30 | 100 | 80 | 100 | 100 | 80 |
| Cotton | 70 | 60 | 50 | 40 | 50 | 60 | 70 | 70 |
| Flax | 80 | 70 | 90 | 100 | 80 | 90 | 40 | 80 |
| Potato | 70 | 30 | 20 | 10 | 10 | 10 | 40 | 10 |
| Soya | 90 | 30 | 30 | 30 | 20 | 30 | 30 | 50 |
| Sugar beet | 30 | 20 | 70 | 0 | 10 | 10 | 0 | 10 |
| Rape | 40 | 20 | 10 | 10 | 30 | 60 | 50 | 40 |
| Sunflower | 60 | 50 | 30 | 80 | 40 | 60 | 90 | 50 |
| Agropyron repens | 70 | 30 | 70 | 50 | 50 | 50 | 30 | 50 |
| Agrostis alba | — | — | — | — | — | — | — | — |
| Alopec. myos. | 80 | 90 | 80 | 70 | 60 | 90 | 80 | 90 |
| Apera sp. venti | 90 | 100 | 100 | 100 | 100 | 100 | 90 | 90 |
| Avena fatua | 90 | 100 | 90 | 80 | 90 | 100 | 100 | 100 |
| Echinochloa c.g.[1] | 80 | 60 | 80 | 80 | 90 | 70 | 80 | 90 |

TABLE C-continued

| Plant treated | Post-emergence application 5 kg/ha Compound Tested - % damage | | | | | | | |
|---|---|---|---|---|---|---|---|---|
| | 25 | 26 | 47 | 48 | 55* | 75 | 84 | 86* |
| c.g.[2] | 90 | 80 | 80 | 90 | 100 | 80 | 90 | 100 |
| Corn | 80 | 60 | 100 | 90 | 30 | 30 | 70 | 80 |
| Wheat | 70 | 90 | 80 | 50 | 10 | 60 | 60 | 80 |
| Rice[2] | 40 | 30 | 10 | 50 | 30 | 30 | 30 | 40 |

*4 kg/ha
[1] upland conditions;
[2] paddy conditions

FIELD TEST

Compound No. 25 has further been evaluated in a pre-emergence Multicrop-Fieldscreening under the following conditions:

| Crops | Soybean ('Steele') - (So) |
| | Cotton ('Stoneville 213') - (Cot) |
| | Corn (LG 11) - (Co) |
| | Wheat (Svenno) - (Wh) |
| Weeds | Alopecurus pratensis - (Al) |
| | Echinochloa crus galli - (Ech) |
| | Galium aparine |
| | Chenopodium album and polyspermum } dicots |
| | Amaranthus retroflexus |

(All the seeds, except for *Alopecurus pratensis* which was sown, were naturally occurring).
Spray volume: 750 lt/ha
Replicates: 3
Evaluation: 28 days after application
Standards: Alachlor (=α-chloro-2',6'-diethyl-N-methoxymethylacetanilide) and Metolachlor [=α-chloro-2'-ethyl-6'-methyl-N-(1-methyl-2-methoxyethyl)acetanilide].
The following herbicidal activity was observed:

| Compound | kg/ha | So | Cot | Co | Wh | Al/Ech | Dicots |
|---|---|---|---|---|---|---|---|
| No. 25 | 0.6 | 0 | 0 | 10 | 63 | 92 | 43 |
| | 1.25 | 3 | 3 | 53 | 80 | 100 | 67 |
| | 2.5 | 5 | 7 | 80 | 92 | 100 | 87 |
| Alachlor | 1.25 | 0 | 0 | 0 | 10 | 43 | 43 |
| | 2.5 | 0 | 3 | 0 | 53 | 78 | 57 |
| Metolachlor | 1.25 | 0 | 0 | 0 | 33 | 100 | 30 |
| | 2.5 | 0 | 0 | 0 | 73 | 100 | 43 |

The above results indicate an herbicidal activity which is equal or superior to that found with commercially available standards against monocotyledonous weeds, and is superior to that of such standards against dicotyledonous weeds. The herbicidal activity is selective in soybean, cotton and at the lowest application rate also in corn.

What is claimed is:
1. A compound of the formula

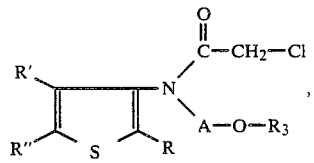

wherein
R and R' are each independently H; F; Cl; Br; $C_{1-4}$alkyl; $C_{1-4}$alkyl substituted by F, Cl, Br, $C_{1-4}$alkoxy $C_{3-6}$cycloalkyl; $C_{2-4}$alkenyl; $C_{2-4}$alkenyl substituted by $C_{1-4}$alkoxy; $C_{3-6}$cycloalkyl; formyl; $C_{2-4}$alkanoyl; $C(=NOC_{1-4}alkyl)$-$C_{1-3}$alkyl; $C(OC_{1-4}alkyl)_2$-$C_{1-3}$alkyl; $CH(OC_{1-4}alkyl)_2$; $C_{1-4}$alkylthio; $C_{1-4}$alkylsulfinyl; $C_{1-4}$alkylsulfonyl; $C_{1-5}$alkoxycarbonyl; $C_{1-4}$alkoxy; $C_{1-4}$alkoxy substituted by F, Cl, Br or $C_{1-4}$alkoxy; $C_{2-4}$alkenyloxy; $C_{2-4}$alkynyloxy; hydroxy; hydroxymethyl; or an ester of hydroxy or hydroxymethyl with formic acid, acetic acid or chloroacetic acid,
R" is H, $C_{1-4}$alkyl, F, Cl, Br or $C_{1-4}$alkoxycarbonyl,
$R_3$ is H or a hydrocarbon group selected from the group consisting of $C_{1-8}$alkyl, $C_{3-8}$alkenyl, $C_{3-8}$alkynyl, $C_{3-8}$cycloalkyl, $C_{5-8}$cycloalkenyl and $C_{3-8}$cycloalkyl-$C_{1-5}$alkyl, said $R_3$ hydrocarbon group being unsubstituted or monosubstituted by F, Cl, Br, cyano or $C_{1-4}$alkoxy, and
A is branched or unbranched $C_{1-8}$alkylene separating the N and O atoms to which it is attached by 1 to 3 carbon atoms.
2. A compound of claim 1 in which both R and R' are other than H.
3. A compound of claim 2 in which A is $CH_2$, $CH_2CH_2$ or a monomethylated derivative thereof and $R_3$ is $C_{1-3}$alkyl.
4. A compound of claim 2 in which $R_3$ is $C_{1-8}$ alkyl.
5. A compound of claim 4 in which R and R' are independently $C_{1-4}$alkyl or $C_{1-4}$alkoxy and R" is H or $C_{1-4}$alkyl.
6. A compound of claim 5 in which A is $CH_2$, $CH_2CH_2$ or a monomethylated derivative thereof and $R_3$ is $C_{1-3}$alkyl.
7. A compound of claim 6 in which R is $CH_3$ or $CH_2CH_3$ and R' is $CH_3$, $CH_2CH_3$, $OCH_3$ or $OCH_2CH_3$.
8. A compound of claim 7 in which R" is H.
9. The compound of claim 8 in which A is $CH(CH_3)CH_2$, $R_3$ is $CH_3$, and R and R' are each methyl.
10. The compound of claim 8 in which A is $CH_2$, $R_3$ is $CH_2CH_3$ and R and R' are each methyl.
11. The compound of claim 8 in which A is $CH_2$, $R_3$ is $CH_2CH_2CH_3$ and R and R' are each methyl.
12. The compound of claim 8 in which A is $CH_2$, $R_3$ is $CH_2CH_3$, R is methyl and R' is ethyl.
13. The compound of claim 8 in which A is $CH_2CH_2$, $R_3$ is $CH_2CH_3$, R is methyl and R' is methoxy.
14. A herbicidal composition, comprising a herbicidally effective amount of a compound of claim 1 in association with an herbicidally acceptable diluent.
15. A method of combatting weeds in a locus which comprises applying to the locus a herbicidally effective amount of a compound of claim 1.
16. The method of claim 15 in which both R and R' are other than H.
17. The method of claim 16 in which A is $CH_2$, $CH_2CH_2$ or a monomethylated derivative thereof, $R_3$ is $C_{1-3}$alkyl, R and R' are independently $C_{1-4}$ alkyl or $C_{1-4}$alkoxy and R" is H or $C_{1-4}$alkyl.
18. The method of claim 17 in which R is $CH_3$ or $CH_2CH_3$, R' is $CH_3$, $CH_2CH_3$, $OCH_3$ or $OCH_2CH_3$ and R" is H.
19. The method of claim 18 in which R and R' are each $CH_3$, A is $CH(CH_3)CH_2$ and $R_3$ is $CH_3$.
20. The method of claim 19 in which the locus is a crop locus and the compound is applied pre-emergence both the crop and weeds in an amount sufficient to combat weeds therein without substantially damaging the crop.

21. The method of claim 20 in which the crop is selected from the group consisting of corn, soybean, cotton, sugar beet, potato, sunflower, rape, peanuts and flax.

22. The method of claim 21 in which the crop is cotton.

23. The method of claim 21 in which the crop is soybean.

24. The method of claim 21 in which the crop is corn.

25. The method of claim 15 in which the locus is a crop locus and the compound is applied pre-emergence to both the crop and weeds in an amount sufficient to combat weeds therein without substantially damaging the crop.

* * * * *